United States Patent [19]

Jabrik et al.

[11] Patent Number: 4,870,220
[45] Date of Patent: Sep. 26, 1989

[54] PROCESS FOR MANUFACTURING METHALLYL CHLORIDE

[75] Inventors: Julius Jabrik, Raesfeld; Gerhard Sticken; Rolf Viehweger, both of Dorsten, all of Fed. Rep. of Germany

[73] Assignee: Huels Aktiengesellschaft, Marl, Fed. Rep. of Germany

[21] Appl. No.: 206,801

[22] Filed: Jun. 15, 1988

[30] Foreign Application Priority Data

Jun. 30, 1987 [DE] Fed. Rep. of Germany ....... 3721472

[51] Int. Cl.$^4$ .................. C07C 17/02; C07C 17/04
[52] U.S. Cl. ..................................... 570/234; 570/216
[58] Field of Search ............... 570/175, 176, 193, 216, 570/234

[56] References Cited

U.S. PATENT DOCUMENTS

| | | | |
|---|---|---|---|
| 2,763,699 | 9/1956 | Van Dijk et al. | 570/234 |
| 3,346,652 | 10/1967 | Pilipovick | 570/175 |
| 3,398,203 | 8/1968 | Olson | 570/175 |
| 4,110,474 | 8/1978 | Lagow et al. | 570/176 |
| 4,754,085 | 6/1988 | Gervasutti et al. | 570/176 |

FOREIGN PATENT DOCUMENTS 62910  5/1975  Japan .

OTHER PUBLICATIONS

"Halogenation of Hydrocarbons", Industrial and Engineering Chemistry, vol. 31, 1939, pp. 1413–1419, Engs et al.

Primary Examiner—Werren B. Lone
Attorney, Agent, or Firm—Oblon, Spivak, McClelland, Maier & Neustadt

[57] ABSTRACT

A method for manufacturing methallyl chloride by reacting isobutene with chlorine in the gas phase is disclosed. The reaction is carried out in a distributed nozzle-mixing reactor which enables the reaction to proceed in a stabile manner even without addition of oxygen. At the same time, the yield of methallyl chloride is increased.

7 Claims, 1 Drawing Sheet

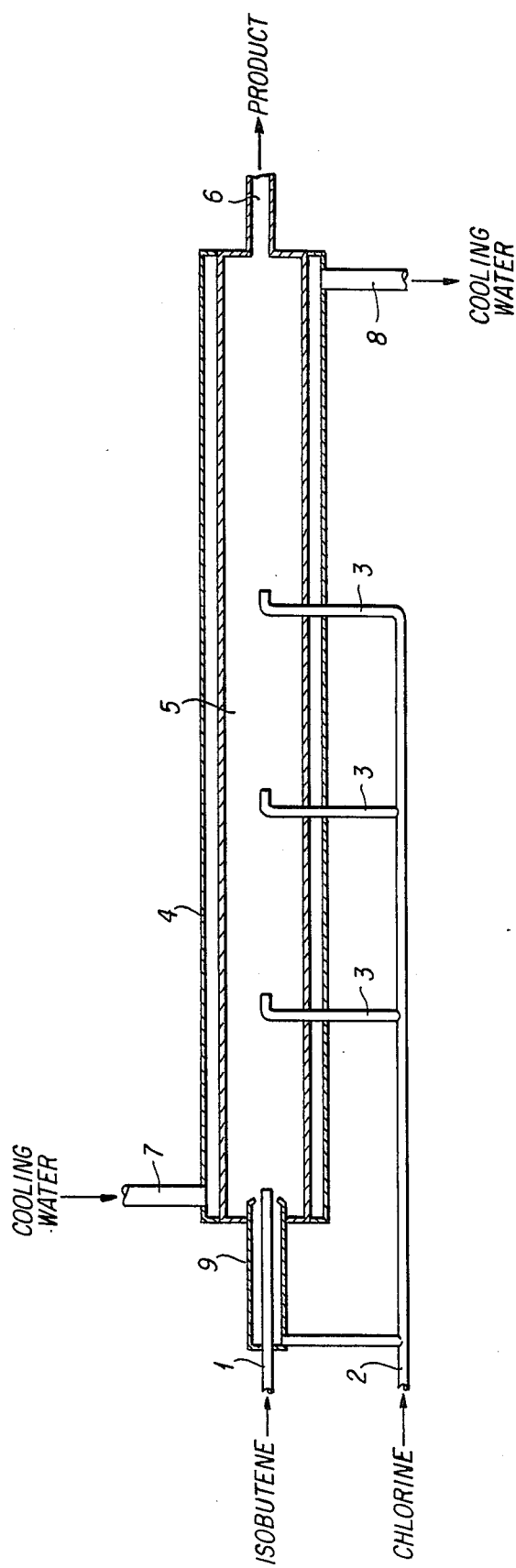

PROCESS FOR MANUFACTURING METHALLYL CHLORIDE

BACKGROUND OF THE INVENTION

1. Field of the Invention

This invention relates to processes for manufacturing methallyl chloride.

2. Discussion of the Background

Methallyl chloride (3-chloro-2-methyl-1-propene) is manufactured industrially by reacting isobutene with chlorine in the gas phase. The reaction is carried out in a cooled tubular reactor at temperatures of c. 100° C. (in particular, under 100° C. to the extent possible) and at approximately atmospheric pressure. The required reaction time is in the range of 0.5 sec. to several seconds. To avoid further chlorinating the methallyl chloride, a slight excess of isobutene is maintained at all times. The starting materials are introduced to the reactor through a nozzle having two outlets.

Attempts to atomize liquid isobutene as an indirect cooling means have no been successful. This technique leads to increased formation of undesirable higher-chlorinated products, evidently a result of poor inter-mixing of the reactants (1975 "Ullmanns Encyklopaedie der technischen Chemie", 4th Ed, pub. Verlag Chemie, Weinheim, Vol. 9, pp. 472 ff.).

Attempts by A. Striegler to prepare methallyl chloride on a laboratory scale from isobutene and chlorine have revealed that irregularities occur in the reaction which are marked by a sudden unexplained temperature rise and result in a marked increase in undesired higher-chlorinated products (1957, "Erfabrungen beider chlorierung von Isobutylen", in *Chem. Techn.*, 9, 523 ff.). Such irregularities have been also observed, with varying frequency and duration, in industrial-scale operations.

These uncontrolled effects can be suppressed by adding certain amounts of oxygen to the reaction mixture. The procedure is set forth in detail in Ger. Pat. No. 3,402,446. Although the amount of oxygen is small according to this method (0.001–1 vol. % based on the volume of the gaseous starting materials), the feed of oxygen can lead to problems, particularly if the oxygen is supplied as air. In particular, the added oxygen exits the reaction system practically unreacted. It is thus present as a "residual gas stream" in the product refinement after the chlorine is washed out and the remaining reaction product is condensed out.

Depending on the refining techniques used, this "residual gas stream" contains chlorinated hydrocarbons and/or unreacted isobutene. Chlorinated hydrocarbons necessitate meeting generally stringent environmental regulations (in the FRG see, e.g., the "Erste Allgemeine Verwaltungsvorschrift zum Bundesimmissionsschutzgesetz", entitled "Technische Anleitung zur Reinhaltung der Luft (TA Luft)" (Edition of 27 Feb. 1986). Unreacted isobutene presents pollution problems and also the problem of keeping the isobutene-oxygen (or isobutene-air) system outside its explosive limits. The presence of chlorinated hydrocarbons and/or unreacted isobutene entails increased costs of manufacturing the methallyl chloride.

There is thus a strongly felt need for a process for producing methallyl chloride which does not suffer the disadvantages of existing processes.

SUMMARY OF THE INVENTION

Accordingly, it is an object of this invention to provide a process for manufacturing methallyl chloride from isobutene and chlorine on an industrial-scale.

It is another object of this invention to provide industrial-scale process for making methallyl chloride, where the process can be performed at a substantially constant temperature.

It is another object of this invention to provide a process for carrying out the reaction of isobutene with chlorine to form methallyl chloride, such that even without introduction of oxygen, which technique is basically very effective, the reaction can be carried out on an industrial scale without problems and at substantially constant temperature.

The inventors have now surprisingly discovered a process for producing methallyl chloride which satisfies all of the above objects of this invention, and other objects which will become apparent from the description of the invention given hereinbelow. This process is characterized in that the reaction of isobutene and chloride is carried out in the gas phase in a distributed nozzle-mixing reactor. In this reactor the isobutene flows through a jacket-cooled reaction tube and the chloride is fed at a plurality of locations on the reaction tube.

BRIEF DESCRIPTION OF THE FIGURE

A more complete appreciation of the invention and many of its attendant advantages will be readily obtained as the same becomes better understood by reference to the following detailed description when considered in connection with the accompanying FIGURE, wherein the FIGURE illustrates an exemplary distributed nozzle-mixing reactor in which the process for producing methallyl chloride, in accordance with the present invention, can be practiced.

DETAILED DESCRIPTION OF THE PREFERRED EMBODIMENTS

The process of the present invention is carried out in a distributed nozzle-mixing reactor. The isobutene component of the reaction flows through a jacket-cooled reaction tube. The chlorine is fed to the reaction area via a plurality of locations on the jacket-cooled reaction tube.

In one preferred embodiment, the chlorine is approximately uniformly distributed among the individual feed locations on the jacket-cooled reaction tube. The chlorine can be fed, for example, at 3 or more feed locations, preferably at from 3 to 5 feed locations.

The feed locations are advantageously chosen such that the amount of chlorine added at any one such location is substantially reacted (e.g. $\geq 60\%$ reacted) before the next such feed location is reached. Preferably, the chlorine feed locations are chosen so that the amount of chlorine added at any one given location is nearly completely converted (e.g. $\geq 95\%$ converted) before the next feed location is reached. The chlorine can be injected at a rate of 150 to 260 m sec$^{-1}$.

Carrying out the reaction in a distributed nozzle-mixing reactor enables the reaction to proceed stabilely even without addition of oxygen. At the same time, the yield of methallyl chloride is increased.

An essential feature of the invention is the use of a "distributed nozzle-mixing reactor" for the manufacture of methallyl chloride from isobutene and chlorine. The distributed nozzle-mixing reactor is characterized in that two (gaseous) reaction components are brought to reaction in a flow tube. One component flows through the tube from beginning to end in its full amount. The other component is added in metered amounts at points distributed along the entire length of the tube. The process is regulated such that the sum of the metered amounts of the second component is the required amount of said second component (see Fitzer, E., and Fritz, W., 1975, "Technische Chemie-Eine Einfuchrung in die chemische Reaktionstechnik", pub. Springer Verlag, Berlin, pp. 75–78 and 322–324).

It has turned out to be surprising, in connection with the present invention, that, in the production of methallyl chloride by reacting isobutene and chlorine in the gas phase, stabile reaction conditions are ensured by the use of a distributed nozzle-mixing reactor, even with no addition of the oxygen employed in existing processes.

In general, isobutene in the gaseous state is passed through a jacket-cooled reaction tube at 0° to 80° C. and pressures of 1 to c. 3 atm (absolute), and the required amount of chlorine (nearly stoichiometric, with, overall, a slight excess of the isobutene) is injected into the isobutene stream at a plurality of points which are preferably uniformly distributed at the individual addition locations.

It has been found, unexpectedly, that this technique leads to a slight increase in the methallyl chloride content, along with a slight decrease in the isocrotyl chloride content of the product outlet stream, compared with the prior technique of introducing isobutene and chlorine simultaneously through a two-substance nozzle at the feed end of the reactor, possibly with pre-addition of oxygen (e.g. pre-addition into the chlorine stream). The result, following refinement of the product (for which see "Ullmanns", loc. cit.), is a measurable increase in the methallyl chloride yield.

This increased yield is appreciable if the total required addition of chlorine is distributed over 3 or more, preferably 3 to 5, feed locations. In each case the chlorine feed locations should be chosen such that the chlorine added to the reaction mixture upstream of a given such location will have been substantially or nearly completely reacted.

To attain high yields of methallyl chloride, it has proven advantageous to inject the chlorine stream via an injection tube which is so narrow that a high injection speed is reached, preferably 150 to 240 m sec$^{-1}$, which is nearly the speed of sound (at 50° C). It is even permissible to inject the chlorine at supersonic speed. However, this is of less commercial interest because of the expense.

Other features of the invention will become apparent in the course of the following descriptions of exemplary embodiments which are given for illustration of the invention and are not intended to be limiting thereof.

Referring now to the FIGURE, wherein like reference numerals designate identical or corresponding parts throughout, the FIGURE illustrates a reactor configuration which can be used in accordance with the present invention. The reactor illustrated is a jacket-cooled tubular reactor having a cooling water inlet 7, a cooling water jacket 4, and a cooling water outlet 8. Isobutene is introduced via pipe 1 into reaction chamber 5 of the reactor. The chlorine is added via pipe 2 to the reaction area via inlets 9 and 3. Inlets 3 are situated along the tubular reactor at three locations in this example, and permit the introduction of chlorine at feed locations chosen such that the chlorine added to the reaction mixture upstream of a given location will have been substantially or nearly completely reacted. The methallyl chloride product exits the tubular reactant via pipe 6.

Comparison Example A

In a 48 m long jacket-cooled tubular reactor, isobutene and chlorine (molar ratio 1.02:1) were reacted to form methallyl chloride, as the main reaction product. The reactants were fed to the reactor through a two-substance nozzle installed at the feed end of the reactor. The pressure in the middle was 1.4 bar (absolute). The reaction was stabilized with 1.20 vol. % air (corresponding to 0.24 vol. % oxygen).

Temperatures of 90°, 87°, 61°, and 46° C. were measured at 4, 8, 12, and 16 m, respectively, along the path of the reaction mixture in the reactor. The condensed, HCl-free reaction product had a methallyl chloride content of 84.2 wt. % and an isocrotyl chloride content of 3.9 wt. %.

After interruption of the air feed, the temperature at the measurement locations mentioned supra increased to 340°, 120°, 72°, and 55° C., respectively. The methallyl chloride content in the condensed reaction product fell to 52.7 wt. %. There was heavy soot deposition in the reactor. The apparatus had to be dismounted and cleaned.

EXAMPLE 1

The preparation of methallyl chloride was carried out as described in Example A, except that the chlorine feed was divided into three equal partial feeds, at lengths 0, 4, and 12 m along the path of the reaction mixture. The feed at point 0 was through the previously used two-substance nozzle. Oxygen was not fed. The speed of the chlorine as it was injected was c. 230 m/sec. The reaction did not display any kind of instability.

The temperatures measured at distances 4, 8, 12, 16, and 24 m were 44°, 79°, 42°, 52°, and 22° C. The condensed reaction product showed a methallyl chloride content of 85.7 wt. % and an isocrotyl chloride content of 3.5 wt. %.

EXAMPLE 2

The preparation of methallyl chloride according to Example 1 was modified in that the necessary amount of chlorine was divided into three equal partial feeds, introduced at lengths 4, 12, and 20 m along the path of the reaction mixture.

Under these conditions the temperatures at 4, 8, 12, 16, and 24 m of reaction distance were 14°, 68°, 40°, 52°, and 52° C., respectively. The methallyl chloride content in the condensed reaction product was 86.5 wt. %, and that of the isocrotyl chloride was 3.5 wt. %. The residual chlorine content analyzed at 12 and 0 m (in each case, immediately upstream of the new injection) showed chlorine conversions of >90%, in both instances (on the basis of total chlorine fed upstream of the given point).

The reaction did not display any kind of instability.

Example 3

The preparation of methallyl chloride according to Example 1 was modified in that the necessary amount of chlorine was divided into four equal partial feeds, introduced at lengths 0, 4, 12, and 20 m along the path of the reaction mixture.

Under this arrangement, the reaction also did not display any kind of instability during its course.

The temperatures measured at 4, 8, 12, 16, and 24 m of reaction distance were 48°, 77°, 42°, 55°, and 54° C., respectively. The methallyl chloride content in the condensed reaction product was 86.5 wt. %, and that of the isocrotyl chloride was 3.4 wt. %.

Example 4

The preparation of methallyl chloride according to Example 1 was modified in that the necessary amount of chlorine was injected as only two equal partial feeds, introduced at lengths of 4 and 20 m along the path of the reaction mixture.

There was no reaction instability observed in this arrangement, either, during the course of the reaction. The temperatures measured at 8, 12, and 24 m were 70°, 58°, and 58° C., respectively. The methallyl chloride content in the condensed reaction product was 85.4 wt. %, and the isocrotyl chloride content was 3.7 wt. %.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for manufacturing methallyl chloride, comprising:
   injecting isobutene, in the gas phase, into a jacket-cooled reaction tube;
   injecting chlorine, in the gas phase, into said jacket-cooled reaction tube at a plurality of feed locations along the length of said jacket-cooled reaction tube; and
   recovering methallyl chloride.

2. The process of claim 1, wherein said chlorine is approximately uniformly distributed among the individual said feed locations.

3. The process of claim 1, wherein the total amount of chlorine used in said process is fed at 3 to 5 different said feed locations.

4. The process of claim 1, wherein said chlorine feed locations are chosen such that the amount of chlorine added at any one such feed location is substantially converted before the next such feed location is reached.

5. The process of claim 1, wherein said chlorine feed locations are chosen such that the amount of chlorine added at any one such feed location is nearly completely converted before the next such feed location is reached.

6. The process of claim 1, wherein said chlorine is injected in said jacket-cooled reaction tube at a speed of from 150 to 260 m sec$^{-1}$.

7. The process of claim 1, wherein the isobutene in the gas phase is injected at a temperature of 0°–80° C. and pressure of 1 to about 3 atmospheres (absolute).

* * * * *